United States Patent [19]

Aida et al.

[11] 4,205,125

[45] May 27, 1980

[54] PROCESS FOR THE PRODUCTION OF COENZYME Q

[75] Inventors: Kô Aida, No. 681-2, Oazanegishi, Urawa-shi, Saitama-ken; Kinya Uchida, Mitaka; Izumi Kawada, Yokohama, all of Japan

[73] Assignee: Ko Aida, Urawa, Japan

[21] Appl. No.: 6,376

[22] Filed: Jan. 25, 1979

Related U.S. Application Data

[63] Continuation-in-part of Ser. No. 935,267, Aug. 21, 1978, abandoned.

[30] Foreign Application Priority Data

Sep. 5, 1977 [JP] Japan ................................ 52-105939

[51] Int. Cl.² ............................................ C12P 7/66
[52] U.S. Cl. ..................................... 435/133; 435/874; 435/877
[58] Field of Search ....................... 195/96, 28 R, 114; 435/133

[56] References Cited

U.S. PATENT DOCUMENTS

3,066,080  11/1962  Folkers et al. ....................... 195/96
3,658,648  4/1972  Nakao et al. ....................... 195/28 R

OTHER PUBLICATIONS

Methods in Enzymology, vol. XVIII Part C, pp. 216-223 (1971).

*Primary Examiner*—Alvin E. Tanenholtz
*Attorney, Agent, or Firm*—Frishauf, Holtz, Goodman & Woodward

[57] ABSTRACT

A process for producing Coenzyme Q which comprises cultivating a microorganism belonging to genus Pseudomonas in a culture medium to which at least one member selected from the group consisting of isopentenyl alcohol (3-methyl-3-butene-1-ol), dimethyl allyl alcohol (3-methyl-2-butene-1-ol), geraniol, isopentenyl acetate, dimethyl allyl acetate, geranyl acetate and β-methyl crotonic acid is added, and obtaining thus formed Coenzyme Q.

9 Claims, No Drawings

PROCESS FOR THE PRODUCTION OF COENZYME Q

This application is a Continuation-In-Part of application Ser. No. 935,267, filed Aug. 21, 1978, now abandoned.

BACKGROUND OF THE INVENTION

1. Field of the Invention

The present invention relates to a process for the production of Coenzyme Q. More particularly, it is concerned with a process for the production of Coenzyme Q which comprises cultivating a microorganism belonging to the genus pseudomonas in a culture medium to which at least one member selected from the group consisting of isopentenyl alcohol, dimethyl allyl alcohol, geraniol, isopentenyl acetate, dimethyl allyl acetate, geranyl acetate and β-methyl crotonic acid is added to form Coenzyme Q and obtaining it.

The term "Coenzyme Q" used in the present invention is generally meant 2,3-dimethoxy-5-methyl-1,4-benzoquinones containing an isoprene side chain in the 6-position of the quinone nucleus represented by the general formula,

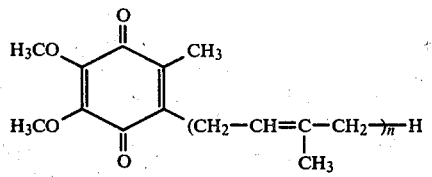

The present invention is intended to provide Coenzyme Q represented by the above formula in which n=8,9 and 10, respectively; that is Coenzyme $Q_8$, Coenzyme $Q_9$ and Coenzyme $Q_{10}$.

Coenzyme Q is widely distributed in animals, plants and microorganisms etc., and it plays an important role as a constitutive element of the terminal electron transfer system.

2. Explanation of the Prior Art

Recently it has been clarified that Coenzyme Q exhibits excellent medical and phisiological activities to various diseases. In particular, Coenzyme $Q_{10}$ is considered most valuable as a medicine since Coenzyme Q of a human being is Coenzyme $Q_{10}$.

It can be considered that the way of obtaining Coenzyme Q is to extract from the animal and plant tissue, or microorganisms, and to synthesize chemically. It is, however, difficult to produce Coenzyme Q by extracting from the animal or plant tissue on a large scale. Also, it is difficult to produce Coenzyme Q by organic synthesis because of a disadvantage in yields. Thus these procedures are not satisfactory for industrial ones. On the other hand, the procedure to extract from microorganisms has the possibility of being employed economically according to the yields of the cells and Coenzyme Q.

It is known that microorganisms belonging to genus Pseudomonas produce Coenzymes $Q_8$, $Q_9$ and $Q_{10}$.

Thus we searched the compounds that were able to markedly increase the content of Coenzyme Q per unit cell when they were added to the culture medium in comparison with the case that they were not added. P-hydroxy benzoic acid, and acetic acid and its salts are known to be able to increase the content of Coenzyme Q per unit cell when added to the culture medium (Japanese Pat. No. 20396/1972). It is known that the isoprene side chain of Coenzyme Q is produced through geranyl- and farnesyl pyrophosphate by the biosynthesis in which the condensation of isopentenyl- and dimethyl allyl pyrophosphate is repeated. However, since these precursors are difficult to permeate through the cell membrane, no attempt to increase the content of Coenzyme Q by adding such precursors to the culture medium has been reported.

SUMMARY OF THE INVENTION

The present invention provides a process for producing Coenzyme Q which comprises cultivating microorganisms belonging to the genus Pseudomonas in a culture medium to which at least one member selected from the group consisting of isopentenyl alcohol, dimethyl allyl alcohol, geraniol, isopentenyl acetate, dimethyl allyl acetate, geranyl acetate and β-methyl crotonic acid is added, to produce Coenzyme Q and obtaining it.

In the present invention, the term "Coenzyme Q" means Coenzyme $Q_8$, $Q_9$ and $Q_{10}$, which are thought to be important from the industrial standpoint.

DETAILED DESCRIPTION OF THE INVENTION

We found that isopentenyl alcohol, dimethyl allyl alcohol, geraniol, isopentenyl acetate, dimethyl allyl acetate, geranyl acetate, and β-methyl crotonic acid were easily utilized by the microorganisms belonging to the genus Pseudomonas when added to the culture medium and that they were able to markedly increase the content of Coenzyme Q per unit cell.

Any of microorganisms belonging to the genus Pseudomonas and capable of producing Coenzyme Q, can be employed in the present invention. For example, these microorganisms capable of producing Coenzyme $Q_{10}$ include Pseudomonas diminuta ATCC 11568 (IAM-1513), etc., those capable of producing Coenzyme $Q_9$ include *Pseudomonas schuylkilliensis* ATCC 31419 (IAM-1126), *Psuedomonas denitrificans* ATCC 13867 (IAM-12023), *Pseudomonas olevorans* ATCC 8062 (IAM-1508), *Pseudomonas putrefaciens* ATCC 8071 (IAM-1509) etc., and those capable of producing Coenzyme $Q_8$ include *Pseudomonas rubescens* ATCC 12099 (IAM-1510), *Pseudomonas fulva* ATCC 31418 (IAM-1529), *Pseudomonas putida* ATCC 4359 (IAM-1506) etc.

In the culture medium used in the practice of the present invention, sugars such as glucose, molasses, etc., and any other carbon sources which these microorganisms are able to utilize, can be used as carbon sources. Inorganic nitrogen compounds such as ammonium sulfate, ammonium chloride and the like, organic nitrogen compounds such as corn steep liquor, extracts of fish meat, peptone, yeast extract, and the like, etc., can be used as nitrogen sources. In addition, as inorganic salts, potassium salts, sodium salts, magnesium salts, salts of phosphoric acid and sulfuric acid and the like, are employed.

The cultivation is usually carried out by agitation with air under the condition of pH 4 to 8, temperature 25 to 35° C. and period 10 to 50 hours.

The addition of isopentenyl alcohol, dimethyl allyl alcohol, geraniol, isopentenyl acetate, dimethyl allyl acetate, geranyl acetate and β-methyl crotonic acid according to the present invention can be carried out by a desired procedure and desired time. For example, all amounts of the additive are added at the start or at a desired growth stage during the cultivation, or it is added little by little according to the state of fermentation. Further, the additive can be used singly or in combination with the other additives. The amount of the additive being added is usually $1 \times 10^{-5}$ to $5 \times 10^{-3}$ mole/liter (as a final concentration), preferably $5 \times 10^{-5}$ to $5 \times 10^{-4}$ mole/liter.

After the cultivation, Coenzyme Q formed is extracted from the cells and separated from other materials. For example, the wet cells obtained by centrifugation are extracted with a hydrophilic solvent, such as acetone and the like; the Coenzyme Q-containing fraction is then transferred into a solvent such as petroleum ether and the like; and the Coenzyme Q-containing fraction is subjected to fractional purification by use of an alumina column, etc., whereby Coenzyme Q can be isolated.

In the present invention, the identification of Coenzyme Q is conducted by comparing the product of this invention with a standard sample by means of UV spectrum, measurement of melting point and reversed phase thin layer chromatography in which a mixture of acetone:water (95:5) is used as a solvent, and others.

The following examples are given to explain the present invention in more detail, but the present invention is not limited by them.

EXAMPLE 1

In a 30 liter-jar fermentor was placed 15 liters of a culture medium (pH 7.0) containing 0.05% of $KH_2PO_4$, 0.15% of $Na_2HPO_4$, 0.05% of $MgSO_4.7H_2O$, 1% of glucose, 1% of peptone and 0.2% of yeast extract. After sterilization with steam, 645 milligrams of isopentenyl alcohol dissolved in 10 milliliters of ethanol was added. *Pseudomonas schuylkilliensis* ATCC 31419 (IAM-1126), which had been previously cultured in 500 milliliters of the culture medium having the same composition as described above for 24 hours, was inoculated in the above culture medium and cultured for 24 hours with aeration of 15 liter/minute at 27° C.

After the cultivation, the culture broth was centrifuged whereby 418 grams of wet cells (87 grams as dry cells) were obtained.

To the wet cells was added 2 liters of acetone, and the extraction was made with stirring. Then the cells were separated by centrifugation. This procedure was repeated two times more. The acetone extracts were combined together and condensed under reduced pressure to distill away the acetone. Thereafter the remaining solution was extracted three times with each 1 liter of petroleum ether respectively and the resulting petroleum ether layers were combined. The combined petroleum ether layer was washed with water, dried over and condensed under reduced pressure. The residual oil was dissolved in a small amount of petroleum ether and subjected to alumina column chromatography by eluting with a mixture of petroleum ether and ethyl ether. The solvent was distilled away from the above obtained eluate containing Coenzyme Q. The residual oil was dissolved in a small amount of ethanol and allowed to stand in a refrigerator whereby crystals of Coenzyme $Q_9$ appeared. These crystals were recrystalyzed from ethanol three times and 142.6 milligrams of crystals of Coenzyme $Q_9$ were obtained.

On the other hand, the same cultivation as above was conducted by use of 15 liters of a culture medium to which no isopentenyl alcohol was added. In the same manner as above, 359 grams of wet cells (69 grams as dry cells) were obtained. Further the same procedure as above was applied whereby 81.42 milligrams of crystals of Coenzyme $Q_9$ were obtained.

Based upon the above data, the effect of iospentenyl alchol on the production of Coenzyme $Q_9$ was calculated. The addition of isopentenyl alcohol to the culture broth increased the yield of Coenzyme $Q_9$ per liter of the broth by 75%, and by 39% per gram of dry cells. Thus it was clearly confirmed that the addition of isopentenyl alcohol was effective to increase the yield of Coenzyme $Q_9$.

EXAMPLE 2

The procedure of Example 1 was followed except that 1.16 grams of geraniol were used in place of isopentenyl alcohol, and 390 milligrams of wet cells (68 grams as dry cells) were obtained. The wet cells were subjected to the same procedure as described in Example 1, and 104.7 milligrams of crystals of Coenzyme $Q_9$ were obtained.

On the other hand, the same microorganism was cultivated by use of the culture medium to which no geraniol was added, and 327 grams of wet cells (63 grams as dry cells) were obtained. From the cells 74.3 milligrams of crystals of Coenzyme $Q_9$ were obtained.

Based upon the above data, the effect of geraniol on the production of Coenzyme Qhd 9 was compared. The addition of geraniol to the culture medium increased the yield of Coenzyme $Q_9$ per liter of the culture broth by 41% and by 30% per gram of the dry cells.

EXAMPLE 3

*Pseudomonas rubescens* ATCC 12099 (IAM-1510) was cultivated in the same culture medium and in the same manner as described in Example 2, and 410 grams of wet cells (73 grams as dry cells) were obtained. These were treated in the same manner as described in Example 1 and 58.4 milligrams of Coenzyme $Q_8$ were obtained.

On the other hand, the same microorganism was cultivated in the same culture medium as above except that no geraniol was added, and 390 grams of wet cells (74 grams as dry cells) were obtained. From the cells, 44.4 milligrams of Coenzyme $Q_8$ were obtained.

Based upon the above data, the same comparison as in Example 1 was made. The addition of geraniol to a culture medium increased the yield of Coenzyme $Q_8$ per liter of the culture broth by 32% and 33% per gram of dry cells.

EXAMPLE 4

*Pseudomonas diminuta* ATCC 11568 (IAM-1513) was cultivated by the same procedure as in Example 1 except that sodium acetate was used in place of glucose in the composition of the medium and three 300 milligrams fractions of isopentenyl alcohol were added separately (total amount 900 milligrams). Thus 380 grams of wet cells (69 grams as dry cells) were obtained, which were then subjected to the same treatment as in Example 1, whereby 30.5 milligrams of crystals of Coenzyme $Q_{10}$ were obtained.

On the other hand, the same microorganism was cultivated in the culture medium to which no isopentenyl alcohol was added, and 320 grams of wet cells (61 grams as dry cells) were obtained, from which 19.8 milligrams of crystals of Coenzyme $Q_{10}$ were obtained.

Based upon the above data, the same comparison as Example 1 was made. The addition of isopentenyl alcohol increased the yield of Coenzyme $Q_{10}$ per liter of the Culture broth by 54% and 38% per gram of dry cells.

EXAMPLE 5

The procedure of Example 1 was followed except that *Pseudomonas denitrificans* ATCC 13867 (IAM-12023) was used as microorganism and that two 1 gram portions of geraniol were added separately to the culture medium (total 2 grams) at different times of cultivation. Thus 395 grams of wet cells (76 grams as dry cells) were obtained, which was then subjected to the same treatment as in Example 1, whereby 63.1 milligrams of crystals of Coenzyme $Q_9$ were obtained.

On the other hand, the same microorganism was cultivated in the culture medium to which no geraniol was added, and 328 grams of wet cells (63 grams as dry cells) were obtained, from which 37.2 milligrams of crystals of Coenzyme $Q_9$ were obtained.

Based upon the above data, the same comparison as in Example 1 was made. The addition of geraniol increased the yield of Coenzyme $Q_9$ per liter of the culture broth by 69% and by 41% per gram of dry cells.

EXAMPLE 6

The procedure of Example 1 was followed except that *Pseudomonas fulva* ATCC 31418 (IAM-1529) was used as microorganism and that three portions of isopentenyl alcohol (total 3 grams) were separately added at different times of cultivation. Thus 390 grams of wet cells (73 grams as dry cells) were obtained, which were then subjected to the same treatment as in Example 1, whereby 86.4 milligrams of crystals of Coenzyme $Q_8$ were obtained.

On the other hand, the same microorganism was cultivated in the culture medium to which no isopentenyl alcohol was added and 350 grams of wet cells (67 grams as dry cells) were obtained, from which 60.5 milligrams crystals of Coenzyme $Q_8$ were obtained.

Based upon the above data, the same comparison as in Example 1 was made. The addition of isopentenyl alcohol increased the yield of Coenzyme $Q_8$ per liter of the culture broth by 43% and by 31% per gram of dry cells.

EXAMPLE 7

The procedure of Example 1 was allowed except that *Pseudomonas rubescens* ATCC 12099 (IAM-1510) was used as microorganism and that 645 milligrams of dimethyl allyl alcohol was added. Thus 430 grams of wet cells (80 grams as dry cells) were obtained, which were subjected to the same treatment as Example 1, whereby 86 milligrams of crystals of Coenzyme $Q_8$ were obtained.

On the other hand, the same microorganism was cultivated in the culture medium to which no dimethyl allyl alcohol was added and 390 grams of wet cells (76 grams as dry cells) were obtained, from which 68 milligrams of crystals of Coenzyme $Q_8$ were obtained.

Based upon the above data, the same comparison as Example 1 was made. By the addition of dimethyl allyl alcohol the yield of Coenzyme $Q_8$ per liter of the culture broth was increased by 26% and by 20% per gram of dry cells.

EXAMPLE 8

The procedure of Example 1 was followed except that *Pseudomonas fulva* ATCC 31418 (IAM-1529) was used as microorganism and that 750 milligrams of β-methyl crotonic acid was added. Thus 540 grams of wet cells (105 grams as dry cells) were obtained, which were subjected to the same treatment as Example 1, whereby 102 milligrams of crystals of Coenzyme $Q_8$ were obtained.

On the other hand, the same microorganism was cultivated in the culture medium to which no β-methyl crotonic acid is added and 525 grams of wet cells (103 grams as dry cells) were obtained, from which 79 milligrams of crystals of Coenzyme $Q_8$ were obtained.

Based upon the above data, the same comparison as in Example 1 was made. The addition of β-methyl crotonic acid increased the yield of Coenzyme $Q_8$ per liter of the culture broth by 28% and by 26% per gram of dry cells.

EXAMPLE 9

The procedure of Example 1 was followed except that *Pseudomonas olevorans* ATCC 8062 (IAM-1508) was used as microorganism and that 960 milligrams of dimethyl allyl acetate was added. Thus 490 grams of wet cells (94 grams as dry cells) were obtained, which were subjected to the same treatment as Example 1, whereby 96 milligrams of crystals of Coenzyme $Q_9$ were obtained.

On the other hand, the same microorganism was cultivated in the culture medium to which no dimethyl allyl acetate was added and 470 grams of wet cells (90 grams as dry cells) were obtained, from which 68 milligrams of crystals of Coenzyme $Q_9$ were obtained.

Based upon the above data, the same comparison as Example 1 was made. The addition of dimethyl allyl acetate increased the yield of Coenzyme $Q_9$ per liter of the culture broth by 42% and by 34% per gram of dry cells.

EXAMPLE 10

The procedure of Example 1 was followed except that *Pseudomonas schuylkilliensis* ATCC 31419 (IAM-1126) was used as the microorganism and that 1.47 grams of geranyl acetate was added. Thus 530 grams of wet cells (93 grams as dry cells) were obtained, which were subjected to the same treatment as Example 1, whereby 120 milligrams of crystals of Coenzyme $Q_9$ were obtained.

On the other hand, the same microorganism was cultivated in the culture medium to which no geranyl acetate was added and 525 grams of wet cells (90 grams as dry cells) were obtained, from which 98 grams of crystals of Coenzyme $Q_9$ were obtained.

Based upon the above data, the same comparison as Example 1 was made. The addition of geranyl acetate increased the yield of Coenzyme $Q_9$ per liter of culture broth by 23% and by 19% per gram of dry cells.

EXAMPLE 11

The procedure of Example 1 was followed except that *Pseudomonas denitrificans* ATCC 13867 (IAM-12023) was used as microorganism and that the mixture of 960 milligrams of isopentenyl acetate and 1.47 grams of geranyl acetate was added. Thus 480 grams of wet cells (96 grams as dry cells) were obtained, which were subjected to the same treatment as Example 1, whereby 115 milligrams of crystals of Coenzyme $Q_9$ were obtained.

On the other hand, the same microogranism was cultivated in the culture medium to which the mixture was not added and 490 grams of wet cells (98 grams as dry cells) were obtained, from which 76 milligrams of crystals of Coenzyme $Q_9$ were obtained.

Based upon the above data, the same comparison as Example 1 was made. The addition of isopentenyl acetate and geranyl acetate increased the yield of Coenzyme $Q_9$ per liter of the culture broth by 51% and by 54% per gram of dry cells.

EXAMPLE 12

*Pseudomonas diminuta* ATCC 11568 (IAM-1513) was cultivated by the same procedure as in Example 4 except that the mixture of 960 milligrams of isopentenyl acetate and 960 milligrams of dimethyl allyl acetate was added. Thus 495 grams of wet cells (98 grams as dry cells) were obtained, which were subjected to the same treatment as Example 1, whereby 53 milligrams of crystals of Coenzyme $Q_{10}$ were obtained.

On the other hand, the same microorganism was cultivated in the culture medium to which the mixture was not added. Thus 480 grams of wet cells (94 grams as dry cells) were obtained, from which 39 milligrams of crystals of Coenzyme $Q_{10}$ were obtained.

Based upon the above data, the same comparison as Example 1 was made. The addition of isopentenyl acetate and dimethyl allyl acetate increased the yield of Coenzyme $Q_{10}$ per liter of culture broth by 36% and by 32% per gram of dry cells.

We claim:

1. In the process for producing Coenzyme $Q_8$–$Q_{10}$ which comprises
   cultivating a microorganism belonging to the genus Pseudomonas in a culture medium to produce Coenzyme $Q_8$–$Q_{10}$, and then recovering said Coenzyme $Q_8$–$Q_{10}$ from the cultivated culture medium, the improvement comprising admixing in said culture medium at least one member selected from the group consisting of isopentenyl alcohol, dimethyl allyl alcohol, geraniol, isopentenyl acetate, dimethyl allyl acetate, geranyl acetate and β-methyl crotonic acid.

2. The process of claim 1, wherein the microorganism is *Pseudomonas diminuta* and the Coenzyme Q produced is Coenzyme $Q_{10}$.

3. The process of claim 1, wherein the microorganism is *Pseudomonas schuylkilliensis* and the Coenzyme Q produced is Coenzyme $Q_9$.

4. The process of claim 1, wherein the microorganism is *Pseudomonas olevorans* and the Coenzyme Q produced is Coenzyme $Q_9$.

5. The process of claim 1, wherein the microorganism is *Pseudomonas denitrificans* and the Coenzyme Q produced is Coenzyme $Q_9$.

6. The process of claim 1, wherein the microorganism is *Pseudomonas rubescens* and the Coenzyme Q produced is Coenzyme $Q_8$.

7. The process of claim 1, wherein the microorganism is *Pseudomonas fulva* and the Coenzyme Q produced is Coenzyme $Q_8$.

8. The process of claim 2, or 3, or 4, or 5, or 6, or 7, or 1 wherein said member which is admixed with said culture medium is in an amount between $1 \times 10^{-5}$ and $5 \times 10^{-3}$ mole per liter as the final concentration of said member in said culture medium.

9. The process of claim 2, or 3, or 4, or 5, or 6, or 7, or 1 wherein said member which is admixed with said culture medium is in an amount between $5 \times 10^{-5}$ and $5 \times 10^{-4}$ mole per liter as the final concentration of said member in said culture medium.

* * * * *